(12) United States Patent
Kobayashi et al.

(10) Patent No.: US 10,131,672 B2
(45) Date of Patent: Nov. 20, 2018

(54) THERAPEUTIC OR PROPHYLACTIC AGENT FOR BILIARY DISEASES

(75) Inventors: Ryosuke Kobayashi, Kamakura (JP); Kaoru Nakao, Kamakura (JP)

(73) Assignee: Toray Industries, Inc. (JP)

( * ) Notice: Subject to any disclaimer, the term of this patent is extended or adjusted under 35 U.S.C. 154(b) by 145 days.

(21) Appl. No.: 13/522,784

(22) PCT Filed: Jan. 28, 2011

(86) PCT No.: PCT/JP2011/051737
§ 371 (c)(1),
(2), (4) Date: Sep. 4, 2012

(87) PCT Pub. No.: WO2011/093441
PCT Pub. Date: Aug. 4, 2011

(65) Prior Publication Data
US 2013/0203797 A1 Aug. 8, 2013

(30) Foreign Application Priority Data
Jan. 29, 2010 (JP) ................................. 2010-018730

(51) Int. Cl.
*C07D 489/00* (2006.01)
*A61K 31/485* (2006.01)
*C07D 489/08* (2006.01)
*C07D 489/02* (2006.01)

(52) U.S. Cl.
CPC .......... *C07D 489/00* (2013.01); *A61K 31/485* (2013.01); *C07D 489/02* (2013.01); *C07D 489/08* (2013.01)

(58) Field of Classification Search
None
See application file for complete search history.

(56) References Cited

U.S. PATENT DOCUMENTS

| | | | | |
|---|---|---|---|---|
| 4,946,848 A * | 8/1990 | Tuttle | .................... | A61K 31/485 514/282 |
| 5,756,745 A * | 5/1998 | Kavka | .................. | C07D 489/08 546/44 |
| 6,174,891 B1 * | 1/2001 | Nagase | .................. | A61K 31/40 514/281 |
| 2003/0054030 A1 * | 3/2003 | Gordon | .................. | A61K 9/127 424/465 |
| 2009/0209569 A1 * | 8/2009 | Arnelle | ................ | C07D 489/08 514/282 |

FOREIGN PATENT DOCUMENTS

| | | | |
|---|---|---|---|
| CA | 2685126 A1 * | 11/2008 | ........... A61K 31/485 |
| EP | 1 380 306 | 1/2004 | |
| JP | 2525552 B2 | 8/1996 | |
| JP | 2000-053572 A | 2/2000 | |
| JP | 2001-163784 A | 6/2001 | |
| WO | 93/15081 A1 | 8/1993 | |
| WO | 95/01178 A1 | 1/1995 | |
| WO | 95/03307 A1 | 2/1995 | |
| WO | 98/23290 A1 | 6/1998 | |
| WO | 99/05146 A1 | 2/1999 | |
| WO | 99/11289 A1 | 3/1999 | |
| WO | 01/14383 A1 | 3/2001 | |
| WO | 02/078744 A1 | 10/2002 | |
| WO | 02/089845 A1 | 11/2002 | |
| WO | 2004/093796 A2 | 11/2004 | |
| WO | 2005/004796 A2 | 1/2005 | |
| WO | 2005/023799 A1 | 3/2005 | |
| WO | 2005/049564 A1 | 6/2005 | |
| WO | 2006/095836 A1 | 9/2006 | |
| WO | 2008/133297 A1 | 11/2008 | |
| WO | 2009/001764 A1 | 12/2008 | |
| WO | WO 2009/132313 | * 10/2009 | |

OTHER PUBLICATIONS

Inan, Nalfurafine, a kappa opioid receptor agonist, inhibits scratching behavior secondary to cholestasis induced by chronic ethynylestradiol injections in rats, Pharmacology, Biochemistry and Behavior, 85:39-43, 2006.*
Guarraci et al., Opioid Agonists Inhibit Excitatory Neurotransmission in Ganglia and at the Neuromuscular Junction in Guinea Pig Gallbladder, Gastroenterology, 122:340-351, 2002.*
Shaffer, Review article: control of gall-bladder motor function, Aliment Pharmacol Ther, 14(2):2-8, 2000.*
Corazziari et al., Functional disorders of the biliary tract and pancreas, Gut, 45(Suppl II):II48-II54, 1999.*
Mela et al. Review article: pruritis in cholestatic and other liver diseases. Aliment Pharmacol Ther 17, 857-870 (2003).*
Venes, D., ed. Taber's Cyclopedic Medical Dictionary, 19th ed. F.A. Davis Company, p. 431 (2001).*
Nogrady et al. Medicinal Chemistry: A Molecular and Biochemical Approach, 3rd ed.. Ch. 1, pp. 9-66 (2005).*
Butler et al. Relief by naloxone of morphine-induced spasm of the sphincter of Oddi in a post-cholecystectomy patient. J. Emerg. Med. 21(2), pp. 129-131 (2001).*

(Continued)

*Primary Examiner* — Jeffrey S Lundgren
*Assistant Examiner* — Michael J Schmitt
(74) *Attorney, Agent, or Firm* — DLA Piper LLP (US)

(57) ABSTRACT

A therapeutic or prophylactic agent for biliary tract diseases includes as an effective component a specific compound having a morphinan skeleton represented by Compound 1, or a pharmaceutically acceptable acid addition salt thereof:

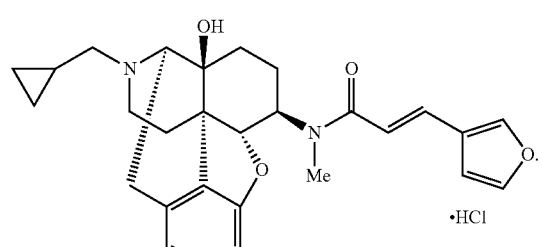

6 Claims, 1 Drawing Sheet

(56) References Cited

OTHER PUBLICATIONS

Bergasa et al. Open-Label Trial of Oral Nalmefene Therapy for the Pruritus of Cholestasis. Hepatology 27(3), pp. 679-684 (1998).*
Terg et al. Efficacy and safety of oral naltrexone treatment for pruritus of cholestasis, a crossover, double blind, placebo-controlled study. J. Hepatology 37, pp. 717-722 (2002).*
Oo et al. Options for Treatment of Primary Biliary Cirrhosis. Drugs 64(20) pp. 2261-2271 (2004).*
Jones et al. The Pruritus of Cholestasis: From Bile Acids to Opiate Agonists. Hepatology 11(5) pp. 884-887 (1990).*
"Morphine Hydrochloride Hydrate," edited and published by *Japan Pharmaceutical Information Center*, available from Maruzen Co., Ltd., JAPIC ethical drugs in Japan 2010, cover, pp. 2705-2710 (1 sheet partial English translation).
"Oxycodone Hydrochloride Hydrate," edited and published by *Japan Pharmaceutical Information Center*, available from Maruzen Co., Ltd., JAPIC ethical drugs in Japan 2010, cover, pp. 618-621 (1 sheet partial English translation).
"Buprenorphine Hydrochloride," edited and published by *Japan Pharmaceutical Information Center*, available from Maruzen Co., Ltd., JAPIC ethical drugs in Japan 2010, cover, pp. 2166-2168 (1 sheet partial English translation).
"Tramadol Hydrochloride," edited and published by *Japan Pharmaceutical Information Center*, available from Maruzen Co., Ltd., JAPIC ethical drugs in Japan 2010, cover, p. 1713 (1 sheet partial English translation).
"Pentazocine," edited and published by *Japan Pharmaceutical Information Center*, available from Maruzen Co., Ltd., JAPIC ethical drugs in Japan 2010, cover, pp. 2448-2450 (1 sheet partial English translation).
"Eptazocine Hydrobromate," edited and published by *Japan Pharmaceutical Information Center*, available from Maruzen Co., Ltd., JAPIC. ethical drugs in Japan 2010, cover, pp. 549-550 (1 sheet partial English translation).
Tamasawa Y. et al., *Kiso to Rinsho*, Nov. 2, 1972, vol. 6, No. 128, pp. 128-132 (1 sheet partial English translation).
J. Behar et al., "Effect of Naloxone on the Cat Sphincter o Oddi (SO): Evidence for a Physiological Role of Opioid Peptides in the Regulation of the Sphincter of Oddi," Motility of the Digestive Tract, 1982, pp. 397-403.
J. Behar et al., "Neural Control of the Sphincter of Oddi: Physiologic Role of Enkephalins on the Regulation of Basal Sphincter of Oddi Motor Activity in the Cat," Gastroenterology, vol. 86, 1984, pp. 134-141.
Teruhiro Yamasato et al., J. Smooth Muscle Res., vol. 27, 1991, pp. 87-96 (Abstract only).
Takeshi Sagara et al., "Design and Synthesis of 10-OXO Derivative of N-Cyclopropylmethyl (−)-6β-Acetylthiodihydro-Normorphine, a Potentially κ-Selective Opioid Receptor Ligand," *Biorganic & Medicinal Chemistry Letters*, vol. 5, No. 14, 1995, pp. 1505-1508.
Holly L. Isenhower et al., "Selection of narcotic analgesics for pain associated with pancreatitis," Am J Health-Syst Pharm, vol. 55, Mar. 1, 1998, pp. 480-486.
Patrick Hastier, MD et al., "First Report of Association of Chronic Pancreatitis, Primary Balmy Cirrhosis, and Systemic Sclerosis," *Digestive Diseases and Sciences*, vol. 43, No. 11, Nov. 1998, pp. 2426-2428.
JG Wei et al., "Dynamic and ultrastructural study of sphincter of Oddi in early-stage cholelithiasis in rabbits with hypercholesterolemia," *World Journal of Gastroenterology*, vol. 6, No. 1, Feb. 2000, pp. 102-106.
Donald R. Thompson, M.D., "Narcotic Analgesic Effects on the Sphincter of Oddi: A Review of the Data and Therapeutic Implications in Treating Pancreatitis," The American Journal of Gastroenterology, vol. 96, No. 4, 2001, pp. 1266-1272.
Anne Marie O'Donnell et al., "Distribution and Chemical Coding of Orphanin FQ/Nociceptin-Immunoreactive Neurons in the Myenteric Plexus of Guinea Pig Intestines and Sphincter of Oddi," The Journal of Comparative Neurology, vol. 430, 2001, pp. 1-11.
Hiromasa Horikiri et al., "Syntheses of 10-Oxo, 10α-Hydroxy, and 10β-Hydroxy Derivatives of a Potent κ-Opioid Receptor Agonist, TRK-820," *Chem. Pharm. Bull.*, vol. 52, No. 6, 2004, pp. 664-669.
Hiromasa Horikiri et al., "A Convenient Oxidation Method of the Benzylic 10-Position in 4,5-Epdxymorphinan," Heterocycles, vol. 63, No. 4, 2004, pp. 865-870.
Saadet Inan et al., "Reduced kappa-opioid activity in a rat model of cholestasis," European Journal of Pharmacology, vol. 518, 2005, pp. 182-186.
Saadet Inan et al., "Nalfurafine, a kappa opioid receptor agonist, inhibits scratching behavior secondary to cholestasis induced by chronic ethynylestradiol injections in rats," Pharmacology, Biochemistry and Behavior, vol. 85, 2006, pp. 39-43.
Humphreys, H., et al., "Opioid-Induced Spasm of the Sphincter of Oddi Apparently Reversed by Nalbuphine," *Anesthesia & Analgesia*, 1992, vol. 74, Issue 2, pp. 308-310.
McMaster, P., "Do Species Lacking a Gall Bladder Possess Its Functional Equivalent?," *The Journal of Experimental Medicine*, Sep. 23, 1921, pp. 127-140.
Examination Report dated Nov. 23, 2017, of corresponding Indian Application No. 2267/KOLNP/2012, along with an English translation.
Malaysian Office Action dated Feb. 15, 2018, of corresponding Malaysian Application No. PI 201700506 in English.
Vatashsky, E., et al., "The Effect of Nalbuphine (Nubain®) Compared to Morphine and Fentanyl on Common Bile Duct Pressure," *Current Therapeutic Research*, vol. 37, No. 1, Jan. 1, 1985. pp. 95-102.

* cited by examiner

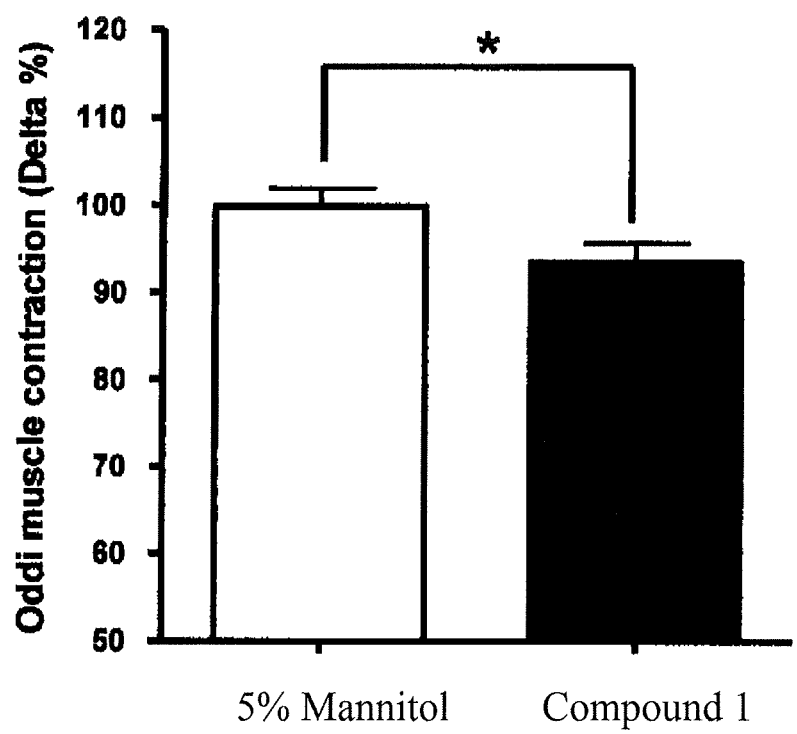

THERAPEUTIC OR PROPHYLACTIC AGENT FOR BILIARY DISEASES

RELATED APPLICATIONS

This is a § 371 of International Application No. PCT/JP2011/051737, with an international filing date of Jan. 28, 2011 (WO 2011/093441 A1, published Aug. 4, 2011), which is based on Japanese Patent Application No. 2010-018730, filed Jan. 29, 2010, the subject matter of which is incorporated by reference.

TECHNICAL FIELD

This disclosure relates to a therapeutic or prophylactic agent for a biliary tract disease(s) comprising as an effective component a morphinan derivative or a pharmaceutically acceptable acid addition salt thereof.

BACKGROUND

The biliary tract disease is a collective term for digestive diseases that occur in the gallbladder, bile duct, pancreas or pancreatic duct. A known example of the cause of occurrence of a biliary tract disease is increased biliary tract pressure due to contraction of sphincter of Oddi in the duodenal papilla, which is the furthest downstream of the biliary tract and corresponds to the distal part of the bile duct formed by confluence of the common bile duct and pancreatic duct. Known examples of the biliary tract disease caused by contraction of sphincter of Oddi include biliary obstruction, gallbladder disorder, cholelithiasis, pancreatitis, biliary dyskinesia, cholangitis and cholecystitis. Therefore, drugs that inhibit contraction of sphincter of Oddi are known to be useful as therapeutic agents for biliary tract diseases caused by contraction of sphincter of Oddi.

Further, examples of biliary tract diseases which are not caused by contraction of sphincter of Oddi, but may be exacerbated by contraction of sphincter of Oddi include primary biliary cirrhosis (which may hereinafter be referred to as "PBC"). PBC is a disease wherein interlobular bile ducts, which are bile ducts positioned upstream of the common bile duct and inside the liver, are destroyed and bile statis occurs. Obstruction of the common bile duct is known to cause exacerbation of PBC (Hastier P et al., Dig Dis Sci., 43, 2426 (1998)). Therefore, it is believed that drugs that inhibit contraction of sphincter of Oddi may ameliorate obstruction of the common bile duct and, hence, inhibit exacerbation of PBC.

Morphinan derivatives and pharmaceutically acceptable acid addition salts thereof, with their κ opioid receptor agonist activity, have been disclosed for uses as analgesics and diuretics (WO 93/015081).

They have already been disclosed for uses in antitussives (WO 95/001178), brain cell protecting agents (WO 95/003307), antipruritics (WO 98/023290), therapeutic agents for hyponatremia (WO 99/005146), ORL-1 receptor antagonists (JP 2000-53572 A), therapeutic agents for neuropathic pain (WO 01/014383), antipruritics for cornea and conjunctiva (JP 2001-163784 A), therapeutic agents for psychoneurotic disorders (WO 02/078744), therapeutic agents for drug dependence (WO 99/011289), therapeutic agents for sepsis (WO 02/089845), therapeutic agents for itching due to multiple sclerosis (WO 06/095836), therapeutic agents for schizophrenia (WO 09/001,764) and therapeutic agents for dyskinesia (WO 08/133,297). However, no therapeutic or prophylactic effect on biliary tract diseases has been disclosed.

Examples of drugs which have actions to inhibit contraction of sphincter of Oddi and are currently used as therapeutic agents for biliary tract diseases include those having actions to promote uptake of $Ca^{2+}$ into intracellular Ca-store sites such as trepibutone, those having actions to inhibit binding of $Ca^{2+}$ in the extracellular fluid to contractile proteins such as hymecromone, those having actions to inhibit catechol-O-methyltransferase (which may hereinafter be referred to as "COMT"), and antiserotonin actions such as flopropione, those having antimuscarinic actions such as tiquizium, those having atropine-like actions and papaverine-like actions such as oxapium, those having trypsin- and kallikrein-inhibition actions although the action mechanism for inhibition of contraction of sphincter of Oddi is unknown such as gabexate. However, these are drugs having neither structural similarity to the above-mentioned compounds nor κ opioid receptor agonist activity.

Further, since opioids are known to cause the contraction of the sphincter of Oddi and may, therefore, exacerbate biliary tract diseases, it is known that use of opioids for patients suffering from biliary tract diseases requires caution. Opioids have been reported as follows.

It is described that since morphine, which has a morphinan skeleton similarly to the compounds mentioned above, but is different from those compounds in view of the fact that it is a μ opioid receptor agonist, may cause biliary tract spasm in patients suffering from a gallbladder disorder or cholelithiasis, it needs to be carefully administered to these patients (JAPIC ethical drugs in Japan 2010, edited and published by Japan Pharmaceutical Information Center, available from Maruzen Co., Ltd., p. 2705, Morphine hydrochloride hydrate).

Further, it is described that since oxycodone, which is a μ opioid receptor agonist having a morphinan skeleton, may cause contraction of sphincter of Oddi and, therefore, exacerbate symptoms in patients suffering from a gallbladder disorder, cholelithiasis or pancreatitis, it needs to be carefully administered to these patients (JAPIC ethical drugs in Japan 2010, edited and published by Japan Pharmaceutical Information Center, available from Maruzen Co., Ltd., p. 618, Oxycodone hydrochloride hydrate). Similarly, it is described that since buprenorphine, which is a μ opioid receptor partial agonist having a morphinan skeleton, causes contraction of sphincter of Oddi in animal experiments (with dogs) at high doses (at not less than 0.1 mg/kg i.v.), it needs to be carefully administered to patients suffering from a biliary tract disease (JAPIC ethical drugs in Japan 2010, edited and published by Japan Pharmaceutical Information Center, available from Maruzen Co., Ltd., p. 2166, Buprenorphine hydrochloride). Further, it is described that since tramadol, which is a μ opioid receptor agonist having no morphinan skeleton, causes contraction of sphincter of Oddi in animal experiments at high doses, it needs to be carefully administered to patients suffering from a biliary tract disease (JAPIC ethical drugs in Japan 2010, edited and published by Japan Pharmaceutical Information Center, available from Maruzen Co., Ltd., p. 1713, Tramadol hydrochloride). Similarly, it is described that since pentazocine, which is a μ opioid receptor partial agonist having no morphinan skeleton, may cause contraction of sphincter of Oddi at high doses, it needs to be carefully administered to patients suffering from a biliary tract disease (JAPIC ethical drugs in Japan 2010, edited and published by Japan Pharmaceutical Information Center, available from Maruzen Co., Ltd., p. 2448, Pentazocine).

It is described that κ opioid receptor agonists having no morphinan skeleton are useful as therapeutic agents for gastrointestinal dysfunction, and examples of the gastrointestinal dysfunction include contraction of sphincter of Oddi (WO 05/004796, WO 05/049564, WO 05/023799 and WO 04/093796). However, there is no description on inhibition of contraction of sphincter of Oddi.

Further, in terms of nalbuphine, which is known to have a morphinan skeleton and to have a κ opioid receptor agonist activity and a μ opioid receptor partial agonist activity, there are a report suggesting that it does not exert any action on contraction of sphincter of Oddi (Isenhower H L et al., Am J Health-Syst Pharm., 55, 480 (1998)) and a report showing that it increases the inner pressure of biliary tract by 6% although the action is not statistically significant (Thompson D R., Am J Gastroenterol., 96, 1266 (2001)). However, there is no report suggesting that nalbuphine inhibits contraction of sphincter of Oddi. Further, since butorphanol, which is classified into a κ opioid receptor agonist, increased the inner pressure of biliary tract by 12% and this action was statistically significant (Thompson D R., Am J Gastroenterol., 96, 1266 (2001)), it has been shown to have contraction of sphincter of Oddi. Further, it is described that since eptazocine, which is known to have no morphinan skeleton but act as a κ agonist on opioid receptors, shows an action to cause contraction of sphincter of Oddi at high doses in animal experiments, it needs to be carefully administered to patients suffering from a biliary tract disease (JAPIC ethical drugs in Japan 2010, edited and published by Japan Pharmaceutical Information Center, available from Maruzen Co., Ltd., p. 549, Eptazocine hydrobromate).

Leucine enkephalin and methionine enkephalin, which are endogenous δ opioid receptor agonist peptides, are reported to cause transient contraction of sphincter of Oddi, followed by showing a continuous contraction inhibition action (Behar J et al., Gastroenterol., 86, 134 (1984)). Further, naloxone, which is a μ opioid receptor antagonist having a morphinan skeleton, is also known to have an action to inhibit contraction of sphincter of Oddi (Behar J et al., Motiltiy of the Digestive Tract, New York: Raven, (1982), p. 397).

Thus, no suggestion has been made at all on inhibition of contraction of sphincter of Oddi by opioid κ receptor agonists having a morphinan skeleton similar to the above-mentioned compounds.

It has been disclosed that the compounds mentioned above show antagonistic actions on the ORL-1 receptor. Since nociceptin (which is sometimes referred to as "orphanin FQ"), which is an endogenous agonist peptide of this receptor, is expressed in the excitatory motor neurons in the myenteric plexus of sphincter of Oddi and inhibits cholinergic neurotransmission, it has been suggested that nociceptin may act on sphincter of Oddi via a feedback autoinhibitory mechanism (O'Donnell A M et al., J Comp Neurol., 29, 430 (2001)).

Thus, ORL-1 receptor agonists are believed to inhibit contraction of sphincter of Oddi, but inhibition of contraction of sphincter of Oddi by an antagonistic action on the ORL-1 receptor has not been suggested.

It could therefore be helpful to provide a therapeutic or prophylactic agent for a biliary tract disease(s) having an excellent effect, which agent comprises as an effective component a specific compound having a morphinan skeleton or a pharmaceutically acceptable acid addition salt thereof.

SUMMARY

We thus provide:
[1] A therapeutic or prophylactic agent for a biliary tract disease(s), the agent comprising as an effective component a compound represented by (I) below:

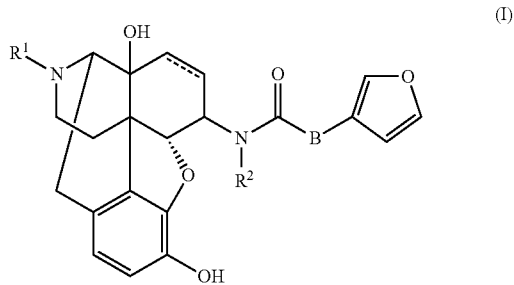

wherein the double line constituted by a dotted line and a solid line represents a double bond or single bond, $R^1$ represents $C_4$-$C_7$ cycloalkylalkyl, $R^2$ represents $C_1$-$C_5$ linear or branched alkyl, and B represents —CH=CH— or a pharmaceutically acceptable acid addition salt thereof
[2] The therapeutic or prophylactic agent for a biliary tract disease(s) according to [1], wherein, in (I), $R^1$ is cyclopropylmethyl, cyclobutylmethyl, cyclopentylmethyl or cyclohexylmethyl, and $R^2$ is methyl, ethyl or propyl.
[3] The therapeutic or prophylactic agent for a biliary tract disease(s) according to [1], wherein the compound represented by (I) is (−)-17-(cyclopropylmethyl)-3,14β-dihydroxy-4,5α-epoxy-6β-[N-methyl-trans-3-(3-furyl)acrylamido]morphinan.
[4] The therapeutic or prophylactic agent for a biliary tract disease(s) according to any one of [1] to [3], wherein the biliary tract disease(s) is/are biliary obstruction, gallbladder disorder, cholelithiasis, pancreatitis, biliary dyskinesia, cholangitis, cholecystitis and/or primary biliary cirrhosis.
[5] The therapeutic or prophylactic agent for a biliary tract disease(s) according to any one of [1] to [3], which agent exerts a therapeutic or prophylactic action on the biliary tract disease(s) by inhibiting contraction of sphincter of Oddi.
[6] A compound represented by (I) below:

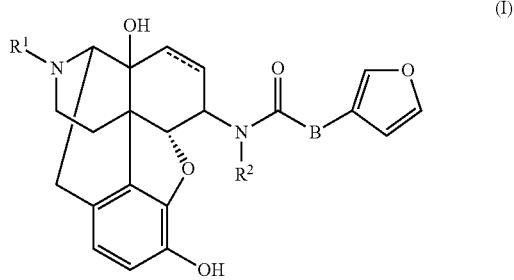

wherein the double line constituted by a dotted line and a solid line represents a double bond or single bond, $R^1$ represents $C_4$-$C_7$ cycloalkylalkyl, $R^2$ represents $C_1$-$C_5$ linear or branched alkyl, and B represents —CH=CH— or a pharmaceutically acceptable acid addition salt thereof, which compound or pharmaceutically acceptable acid addition salt is used for therapy or prophylaxis of a biliary tract disease(s).

[7] A method of therapy or prophylaxis of a biliary tract disease(s), the method comprising administering an effective amount of a compound represented by (I) below:

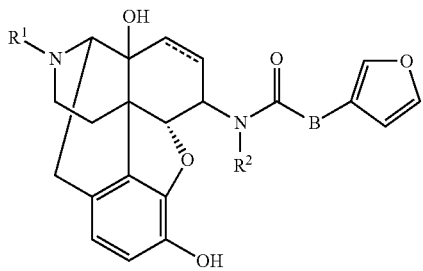

(I)

wherein the double line constituted by a dotted line and a solid line represents a double bond or single bond, $R^1$ represents $C_4$-$C_7$ cycloalkylalkyl, $R^2$ represents $C_1$-$C_5$ linear or branched alkyl, and B represents —CH=CH— or a pharmaceutically acceptable acid addition salt thereof to a patient who needs a therapeutic or prophylactic agent for a biliary tract disease(s).

We thus provide a remarkable therapeutic or prophylactic effect on biliary tract diseases.

BRIEF DESCRIPTION OF THE DRAWING

FIG. 1 is a diagram showing the influence of Compound 1 on contraction of sphincter of Oddi in rabbit in Example 1. The abscissa indicates a test substance, and the ordinate indicates the rate of change in the maximum perfusion pressure (Oddi muscle contraction (Delta %)) based on comparison between the value observed during the 3 minutes immediately before beginning of intravenous administration of the test substance and the value observed during the 3 minutes immediately after the beginning of administration (mean±standard error; N=11 cases, *p<0.05, paired t-test).

DETAILED DESCRIPTION

The therapeutic or prophylactic agent for a biliary tract disease(s) comprises as an effective component a compound represented by (III) or a pharmaceutically acceptable acid addition salt thereof:

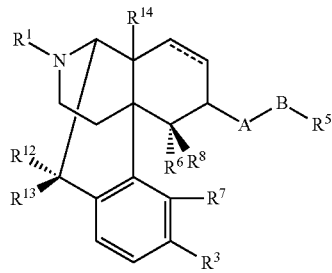

(III)

wherein the double line constituted by a dotted line and a solid line represents a double bond or single bond, $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, furan-2-ylalkyl (the alkyl moiety has 1 to 5 carbon atom(s)), or thiophen-2-ylalkyl (the alkyl moiety has 1 to 5 carbon atom(s)), $R^{14}$ represents hydrogen, hydroxy, nitro, $C_1$-$C_5$ alkanoyloxy, $C_1$-$C_5$ alkoxy, $C_1$-$C_5$ alkyl or $NR^9R^{10}$. Here, $R^9$ represents hydrogen or $C_1$-$C_5$ alkyl, $R^{10}$ represents hydrogen, $C_1$-$C_5$ alkyl or —(C=O)$R^{11}$, $R^{11}$ represents hydrogen, phenyl or $C_1$-$C_5$ alkyl, $R^3$ represents hydrogen, hydroxy, $C_1$-$C_5$ alkanoyloxy or $C_1$-$C_5$ alkoxy, A represents —XC(=Y)—, —XC(=Y)Z—, —X— or —XSO$_2$— (wherein X, Y and Z each independently represent $NR^4$, S or O, wherein $R^4$ represents hydrogen, $C_1$-$C_5$ linear or branched alkyl or $C_6$-$C_{12}$ aryl, and, in cases where two or more $R^4$ exist in the formula, these may be the same or different), B represents a valence bond, $C_1$-$C_{14}$ linear or branched alkylene (which may be substituted by at least one substituent selected from the group consisting of $C_1$-$C_5$ alkoxy, $C_1$-$C_5$ alkanoyloxy, hydroxy, fluorine, chloro, bromo, iodo, amino, nitro, cyano, trifluoromethyl and phenoxy, and 1 to 3 methylene group(s) may be substituted by carbonyl); $C_2$-$C_{14}$ linear or branched acyclic unsaturated hydrocarbon comprising 1 to 3 double bond(s) and/or triple bond(s) (which may be substituted by at least one substituent selected from the group consisting of $C_1$-$C_5$ alkoxy, $C_1$-$C_5$ alkanoyloxy, hydroxy, fluorine, chloro, bromo, iodo, amino, nitro, cyano, trifluoromethyl and phenoxy, and 1 to 3 methylene group(s) may be substituted by carbonyl); or $C_1$-$C_{14}$ linear or branched, saturated or unsaturated hydrocarbon comprising 1 to 5 thioether bond(s), ether bond(s) and/or amino bond(s) (wherein no heteroatom is directly bound to A, and 1 to 3 methylene group(s) may be substituted by carbonyl), $R^5$ represents hydrogen or an organic group having any of the following basic skeletons (wherein Q represents N, O or S; T represents $CH_2$, NH, S or O; l represents an integer of 0 to 5; m and n each independently represent an integer of 0 to 5; the sum of m and n is not more than 5; and each organic group may be substituted by at least one substituent selected from the group consisting of $C_1$-$C_5$ alkyl, $C_1$-$C_5$ alkoxy, $C_1$-$C_5$ alkanoyloxy, hydroxy, fluorine, chloro, bromo, iodo, amino, nitro, cyano, isothiocyanato, trifluoromethyl, trifluoromethoxy and methylenedioxy),

 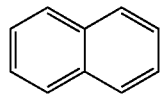 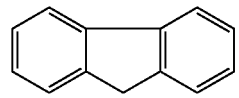

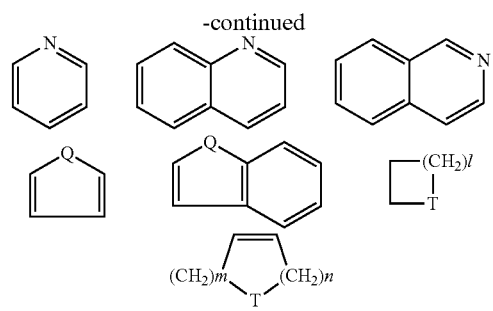

Q: N, O, S
T: CH$_2$, NH, S, O
l = 0-5
m, n ≥ 0
m + n ≤ 5

Organic groups represented by R$^5$

R$^6$ represents hydrogen, and R$^7$ represents hydrogen, hydroxy, C$_1$-C$_5$ alkoxy or C$_1$-C$_5$ alkanoyloxy; or R$^6$ and R$^7$ together represent —O—, —CH$_2$— or —S—, R$^8$ represents hydrogen, C$_1$-C$_5$ alkyl or C$_1$-C$_5$ alkanoyl, R$^{12}$ and R$^{13}$ together represent hydrogen; one of these represents hydrogen and the other represents hydroxy; or these together represent oxo, (III) includes (+), (−) and (±) isomers.

The double line constituted by a dotted line and a solid line in (III) represents a double bond or single bond, and the double line preferably represents a single bond.

The therapeutic or prophylactic agent for a biliary tract disease(s) preferably comprises, among the compounds represented by (III) and pharmaceutically acceptable acid addition salts thereof, a compound represented by the above-described (I) or a pharmaceutically acceptable acid addition salt thereof as an effective component.

The double line constituted by a dotted line and a solid line in (I) represents a double bond or single bond, and the double line preferably represents a single bond.

In (I), R$^1$ represents C$_4$-C$_7$ cycloalkylalkyl. Among these, R$^1$ is preferably cyclopropylmethyl, cyclobutylmethyl, cyclopentylmethyl or cyclohexylmethyl, especially preferably cyclopropylmethyl.

R$^2$ represents C$_1$-C$_5$ linear or branched alkyl. R$^2$ is preferably methyl, ethyl or propyl. Among these, methyl is more preferred.

B represents —CH=CH—. B is preferably trans —CH=CH—.

The compound represented by (I) is especially preferably a (−)-compound wherein the double line constituted by a dotted line and a solid line represents a single bond; R$^1$ represents cyclopropylmethyl; R$^2$ represents methyl; and B represents trans —CH=CH—. That is, the compound represented by (I) is especially preferably (−)-17-(cyclopropylmethyl)-3,14β-dihydroxy-4,5α-epoxy-6β-[N-methyl-trans-3-(3-furyl)acrylamido]morphinan. However, the agent is not restricted thereto.

These compounds represented by (I) and pharmaceutically acceptable acid addition salts thereof can be produced according to the method described in JP 2525552 B. Among the compounds represented by (III), those wherein R$^{12}$ and R$^{13}$ together represent hydrogen can be produced according to the method described in JP 2525552 B. Among the compounds represented by (III), those wherein R$^{12}$ and R$^{13}$ together represent oxo can be produced by, for example, using, as a starting material, a compound having 10-oxo obtained according to a document (Heterocycles, 63, 865 (2004), Bioorg. Med. Chem. Lett., 5, 1505 (1995)) and following the methods described in Chem. Pharm. Bull., 52, 664 (2004) and JP 2525552 B. Further, among the compounds represented by (I), those wherein R$^{12}$ represents hydroxy and R$^{13}$ represents hydrogen can be produced according to the method described in Chem. Pharm. Bull., 52, 664 (2004).

Examples of the pharmaceutically acceptable acid addition salt include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferably used, but, needless to say, the pharmaceutically acceptable acid addition salt is not restricted thereto.

The "biliary tract disease" includes digestive diseases that occur in the gallbladder, bile duct, pancreas or pancreatic duct. Among these, the therapeutic or prophylactic agent for a biliary tract disease(s) is preferably applicable to a biliary tract disease(s) that occur(s) and/or exacerbate(s) due to contraction of sphincter of Oddi, especially preferably biliary obstruction, gallbladder disorder, cholelithiasis, pancreatitis, biliary dyskinesia, cholangitis, cholecystitis, primary biliary cirrhosis and/or the like.

The compound represented by (I) or a pharmaceutically acceptable acid addition salt thereof is purified to a level suitable for medical use and, after passing a necessary safety test, the compound or acid addition salt may be orally or parenterally administered as it is or as a pharmaceutical composition prepared as a mixture with a known pharmaceutically acceptable acid(s), carrier(s), vehicle(s) and/or the like. Examples of its formulation include tablets, capsules, orally disintegrating tablets, powders and granules in the case of oral administration; and formulations for intravenous rapid infusion, intravenous sustained infusion, intramuscular injection, subcutaneous injection or intradermal injection, and tapes and patches, in the case of parenteral administration. However, the formulation is of course not limited thereto.

The content of the compound represented by (I) or a pharmaceutically acceptable acid addition salt thereof is not restricted, and the compound or acid addition salt may be usually prepared such that the dose per administration is 0.1 μg to 100 mg. The dose may be appropriately selected depending on the symptoms, age and body weight of the patient, administration method and/or the like, and the dose per adult per day is usually about 0.1 μg to 20 mg, preferably about 1 μg to 10 mg in terms of the amount of the compound represented by (I) or a pharmaceutically acceptable acid addition salt thereof, which may be administered at once or in several times.

As the therapeutic or prophylactic agent for a biliary tract disease(s), the compound represented by (I) or a pharmaceutically acceptable acid addition salt thereof may be administered either alone or in combination with one or more drugs which are used for therapy or prophylaxis of a disease(s), or for alleviation or inhibition of a symptom(s).

Examples of the drugs include cholagogues such as trepibutone (therapeutic agent for pancreatic/biliary tract diseases), hymecromone (therapeutic agent for biliary tract diseases), flopropione (pancreaticobiliar/urinary tract antispasmodic), tiquizium (antimuscarinic agent), oxapium (antispasmodic anticholinergic agent), gabexate (protease inhibitor), dehydrocholic acid, anetholtrithion, ursodeoxycholic acid and chenodeoxycholic acid.

Examples of the drugs also include morphine, pentazocine, buprenorphine, oxycodone, fentanyl, remifentanil, tramadol, butorphanol and eptazocine, which are drugs to be administered for alleviation of pain due to biliary tract diseases and, at the same time, having side effects that promote contraction of sphincter of Oddi. It is also possible, by combining these drugs with our agent, to suppress side effects.

These are merely examples and should not be interpreted in any restrictive way. The method for combining the drugs may be either combined use of the drugs or use of the drugs as a mixture.

The fact that a compound represented by (I) or a pharmaceutically acceptable acid addition salt thereof as an effective component of the therapeutic or prophylactic agent is effective for therapy and/or prophylaxis of a biliary tract disease(s) can be confirmed by the method described in Examples below. The rabbit model for contraction of sphincter of Oddi is commonly used in basic research on biliary tract diseases (Wei J G et al., World J. Gastroenterol., 6, 102 (2000)), and, in cases where the drug shows an action to inhibit contraction of sphincter of Oddi in this model, the drug can be said to have a therapeutic and/or prophylactic effect on biliary tract diseases.

EXAMPLES

Our agents and methods will now be described concretely by way of an Example.

Example 1

Effect of (−)-17-(cyclopropylmethyl)-3,14β-dihydroxy-4,5α-epoxy-6β-[N-methyl-trans-3-(3-furyl) acrylamido]morphinan hydrochloride (Compound 1) on the Contraction of Sphincter of Oddi in Rabbits The method described in Wei J G et al., World J. Gastroenterol., 6, 102 (2000) was partially modified and used for measurement of a change in the perfusion pressure in sphincter of Oddi. The change in the perfusion pressure reflects the motility of a contractive change of sphincter of Oddi.

Male NZW rabbits (Japan SLC) which had body weights of 2.0 to 2.5 kg upon delivery were fasted from the evening of the day before the experiment. The experiment was carried out under anesthesia with pentobarbital, with artificial ventilation. Each rabbit was immobilized in the supine position and subjected to abdominal incision to expose the periduodenal area and the common bile duct. A small incision was made in the common bile duct, and a cannula was inserted into the common bile duct toward the duodenum side, followed by indwelling its tip in sphincter of Oddi (sphincter ampullae). For biliary excretion, another cannula was inserted into the bile duct toward the gallbladder side and immobilized. From the other end of the cannula whose tip was indwelled in the sphincter of Oddi, physiological saline was continuously injected at a flow rate of 6 mL/hour to allow perfusion in the sphincter of Oddi. By recording the perfusion pressure with a blood pressure monitoring transducer (DX-300, Nihon Kohden Corporation), the contraction reaction of sphincter of Oddi was measured.

To the rabbit, 5% aqueous mannitol solution, which is the vehicle for the Compound 1 solution, was administered via the jugular vein. Further, not less than 30 minutes after the administration of the vehicle, Compound 1 was administered to the same individual at a dose of 0.2 µg/kg via the jugular vein. The administration volume of the vehicle and Compound 1 was 1 mL/kg, and the administration was carried out for 60 seconds.

FIG. 1 shows the result of calculation of the rate of change in the maximum perfusion pressure (Oddi muscle contraction (Delta %)) based on comparison between the value observed during the 3 minutes immediately before beginning of the administration and the value observed during the 3 minutes immediately after beginning of the administration (mean±standard error; N=11 cases). In contrast to the fact that the rate of change in the maximum perfusion pressure was 93.32% on average in the case of intravenous administration of 0.2 µg/kg Compound 1, the rate of change in the maximum perfusion pressure was 99.81% on average in the case of administration of the vehicle. Thus, in the Compound 1-administered group, the rate of change in the maximum perfusion pressure was lower compared to the vehicle-administered group, and this difference was significant (*p<0.05, paired t-test). This indicates that Compound 1 has an action to inhibit contraction of sphincter of Oddi.

Oxapium iodide, which has an action to inhibit contraction of sphincter of Oddi and is currently clinically used as a therapeutic agent for biliary tract diseases, reduces the sphincter of Oddi perfusion pressure by about 10 mmH$_2$O (corresponds to 0.74 mmHg) when it is intravenously administered to a dog at a dose of 0.3 mg/kg (Tamasawa Y. et al., Kiso to Rinsho, 6, 128 (1972)). Further, gabexate mesilate reduces the sphincter of Oddi perfusion pressure by 6.9 mmH$_2$O (corresponds to 0.51 mmHg) or 10.6 mmH$_2$O (corresponds to 0.78 mmHg) when it is intravenously administered to a dog at a dose of 1 mg/kg or 3 mg/kg, respectively (Yamasato T. et al., J Smooth Muscle Res., 27, 87 (1991). Since oxapium iodide is usually orally administered at a dose of 30 to 60 mg per adult per day dividedly in 3 times, and 100 mg of gabexate mesilate is usually dissolved in 500 mL of Ringer's solution and the resulting solution is administered by intravenous drip infusion at a rate of not more than 8 mL/minute, the above-described doses are considered to be equivalent to the clinical doses of those drugs.

In this Example, by intravenous administration of 0.2 µg/kg of Compound 1 to rabbits, the actual value of the maximum perfusion pressure was reduced by 0.95 mmHg on average. This result therefore indicates that, by using Compound 1, a therapeutic and prophylactic effect on biliary tract diseases can be clinically expected.

Compound 1 has a structure represented by (II) below:

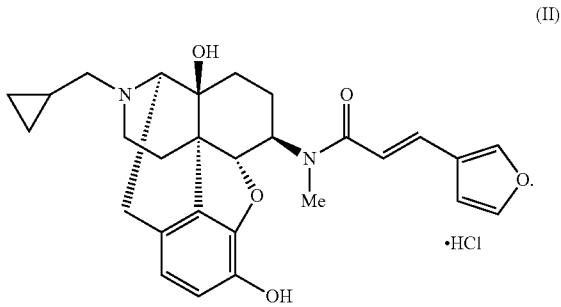 [SMILES: CN(C(=O)/C=C/c1ccoc1)[C@@H]1CC[C@@]2(O)[C@H]3Cc4ccc(O)c5c4[C@@]2(CCN3CC2CC2)[C@H]1O5 ; Cl]

(II)

INDUSTRIAL APPLICABILITY

We provide an excellent therapeutic effect on biliary tract diseases and is useful for therapy and/or prophylaxis of biliary tract diseases.

The invention claimed is:

1. A method of treating a biliary tract disease(s) selected from the group consisting of biliary obstruction, gallbladder disorder, cholelithiasis, pancreatitis, biliary dyskinesia, cholangitis, cholecystitis and primary biliary cirrhosis comprising administering an effective amount of a compound represented by (I) below:

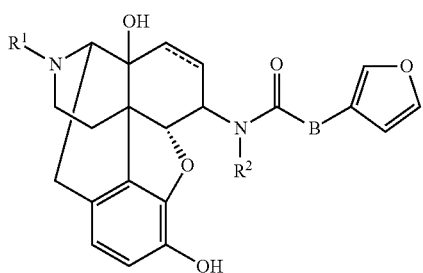

wherein the double line constituted by a dotted line and a solid line represents a double bond or single bond, $R^1$ represents $C_4$-$C_7$ cycloalkylalkyl, $R^2$ represents $C_1$-$C_5$ linear or branched alkyl, and B represents —CH=CH— or a pharmaceutically acceptable acid addition salt thereof to a patient with a gallbladder who has a biliary tract disease(s) that occur(s) and/or is/are exacerbated by the contraction of the sphincter of Oddi and is suffering from pathological contraction of the sphincter of Oddi.

2. The method according to claim 1, wherein, in (I), $R^1$ is cyclopropylmethyl, cyclobutylmethyl, cyclopentylmethyl or cyclohexylmethyl, and $R^2$ is methyl, ethyl or propyl.

3. The method according to claim 1, wherein said compound represented by (I) is (−)-17-(cyclopropylmethyl)-3,14β-dihydroxy-4,5α-epoxy-6β-[N-methyl-trans-3-(3-furyl)acrylamido]morphinan.

4. The method according to claim 1, wherein a dosage per administration is 0.1 μg to 100 mg of the compound or the pharmaceutically acceptable acid addition salt thereof.

5. The method according to claim 1, wherein a means of administration of the compound is orally or parenterally.

6. The method according to claim 1, wherein a dosage per administration is 0.2 μg/kg body weight of the compound or the pharmaceutically acceptable acid addition salt thereof.

* * * * *

UNITED STATES PATENT AND TRADEMARK OFFICE
CERTIFICATE OF CORRECTION

PATENT NO. : 10,131,672 B2
APPLICATION NO. : 13/522784
DATED : November 20, 2018
INVENTOR(S) : Kobayashi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 139 days.

Signed and Sealed this
Twenty-seventh Day of August, 2019

Andrei Iancu
*Director of the United States Patent and Trademark Office*